United States Patent [19]

Nair et al.

[11] Patent Number: 5,145,854
[45] Date of Patent: Sep. 8, 1992

[54] 10-FORMYL-5,8,10-TRIDEAZAFOLATES

[76] Inventors: Madhavan G. Nair, 7005 Charleston Oaks Dr. North, Mobile, Ala. 36695; Shu W. Li, 5811 Old Shell Road, Apt. B, Mobile, Ala. 36608

[21] Appl. No.: 799,166

[22] Filed: Nov. 27, 1991

[51] Int. Cl.$^5$ .................. C07D 401/02; A61K 31/505
[52] U.S. Cl. .................... 514/259; 514/249; 514/260; 514/258 544/258; 544/279; 544/287
[58] Field of Search ............... 544/287; 514/259, 260

[56] References Cited

U.S. PATENT DOCUMENTS

| | | | |
|---|---|---|---|
| 3,472,851 | 10/1984 | Davoll | 544/287 |
| 4,447,608 | 5/1984 | Jones et al. | 544/287 |
| 4,857,530 | 8/1989 | Berman et al. | 544/287 |
| 4,889,859 | 12/1989 | Taylor et al. | 514/258 |
| 4,981,856 | 1/1991 | Hughes et al. | 544/287 |
| 4,992,550 | 2/1991 | Hughes | 544/287 |

FOREIGN PATENT DOCUMENTS

| | | |
|---|---|---|
| 318225 | 5/1989 | European Pat. Off. |
| 373891 | 6/1990 | European Pat. Off. |
| 2065653 | 7/1981 | United Kingdom |

OTHER PUBLICATIONS

Nair, Nanavati et al. J. Med. Chem 29, 1754, 1986.
Nair et al. J. Med. Chem 30, 1256, 1987.

*Primary Examiner*—Donald G. Daus

[57] ABSTRACT

A 10-deaza-10-formyl folate analogue is a potent inhibitor of the enzyme glycinamide ribonucleotide formyltransferase and an antitumor agent. A typical embodiment is 10-formyl-5,8,10-trideazafolic acid (FTDF).

6 Claims, No Drawings

1-FORMYL-5,8,10-TRIDEAZAFOLATES

FIELD OF THE INVENTION

This invention relates to anticancer agents and the process for their manufacture.

ORIGIN OF THE INVENTION

The invention described herein was in part made in the course of work under a grant (CA 27101) from the National Institutes of Health, Department of Health, Education and Welfare.

Cancer is a neoplastic disease of man which is characterized by uncontrolled cell division, and tissue destruction, that can be treated effectively with antifolate drugs. The most well known antifolate anticancer drug is methotrexate (MTX), which is a folate antagonist that inhibits the folate-based enzyme dihydrofolate reductase (DHFR). Inhibitors of DHFR are widely used in the chemotherapy of neoplastic and infectious diseases (Nair, M. G.; Chemistry of Antitumor Agents, Blackie and Sons. London; Chapman and Hall. USA. 1990, Chapter 7). Methotrexate is used in the chemotherapy of cancer, either as a single agent or in combination with other drugs. MTX interferes with folate metabolism at the stage of reductive regeneration of tetrahydrofolate from dihydrofolate; thus depriving the cells of this essential vitamin for growth. Depletion of tetrahydrofolate results in a generalized blockade of one carbon metabolism. (Nair, M. G., Cancer Growth and Progression. Cancer Management in Man. Kluwer Academic Publishers, 1989, Chapter 4). Classical antifolates such as MTX and the 10-deazaaminopterins are metabolized to their respective poly-y-glutamates. (Nair and Baugh; Biochemistry 12:3923, 1973; Nair, Nanavti, et al. J. Med. Chem. 31:181, 1988) and these non-effluxible metabolites and in turn directly inhibits the folate-based enzymes thymidylate synthase and AICARformyltransferase [(Kisliuk, et al. Chemistry and Biology of Pteridines, Elsevier North Holland, 1979, p. 261) (Allegra et al. Proc. Natl. Acad. Sci, (USA) 82, 4881, 1985)] thus potentiating their toxicity. Although classical folate analogues, that are inhibitors of DHFR are effective anticancer agents, the clinical utility of these agents are rather limited due to a total blockade of one carbon metabolism and the resultant host toxicity. The recently developed non-polyglutamatable DHFR inhibitors are envisioned to be more specific for their target enzyme and less toxic (Nair and Abraham, U.S. Pat. No. 4,996,207, 1991) but their clinical potential remains to be established. Recently, Taylor and coworkers identified another folate-based enzyme, glycinamide ribonucleotide formyl transferase (GARFTase) as an attractive target for anticancer agents (Taylor, et al. U.S. Pat. No. 4,684,653; 1987; Taylor and Shih, U.S. Pat. No. 4,889,859; 1989). Tumor cells that are highly proliferative, have a larger demand for purine nucleotide substrates for DNA synthesis, relative to normal cells, and this demand is met by the denovo purine biosynthetic pathway as opposed to the salvage pathway. GARFTase is an enzyme that participate in the denovo purine biosynthesis, and an effective inhibitor of this enzyme is expected to exhibit selective tumor toxicity. In conformity with this prediction, two potent inhibitors of GARFTase were shown to exhibit a wide spectrum of antitumor activity. These inhibitors are 5,10-dideazatetrahydrofolic acid (DDATHF) and 5-deazaacyclotetrahydrofolic acid (5-DACTHF) (Taylor, J. Hetrocyclic Chem. 27, 1-12, 1990; Smith et al. Chemistry and Biology of Pterdines, Walter de Gruyter, 1015, 1990).

5,145,854
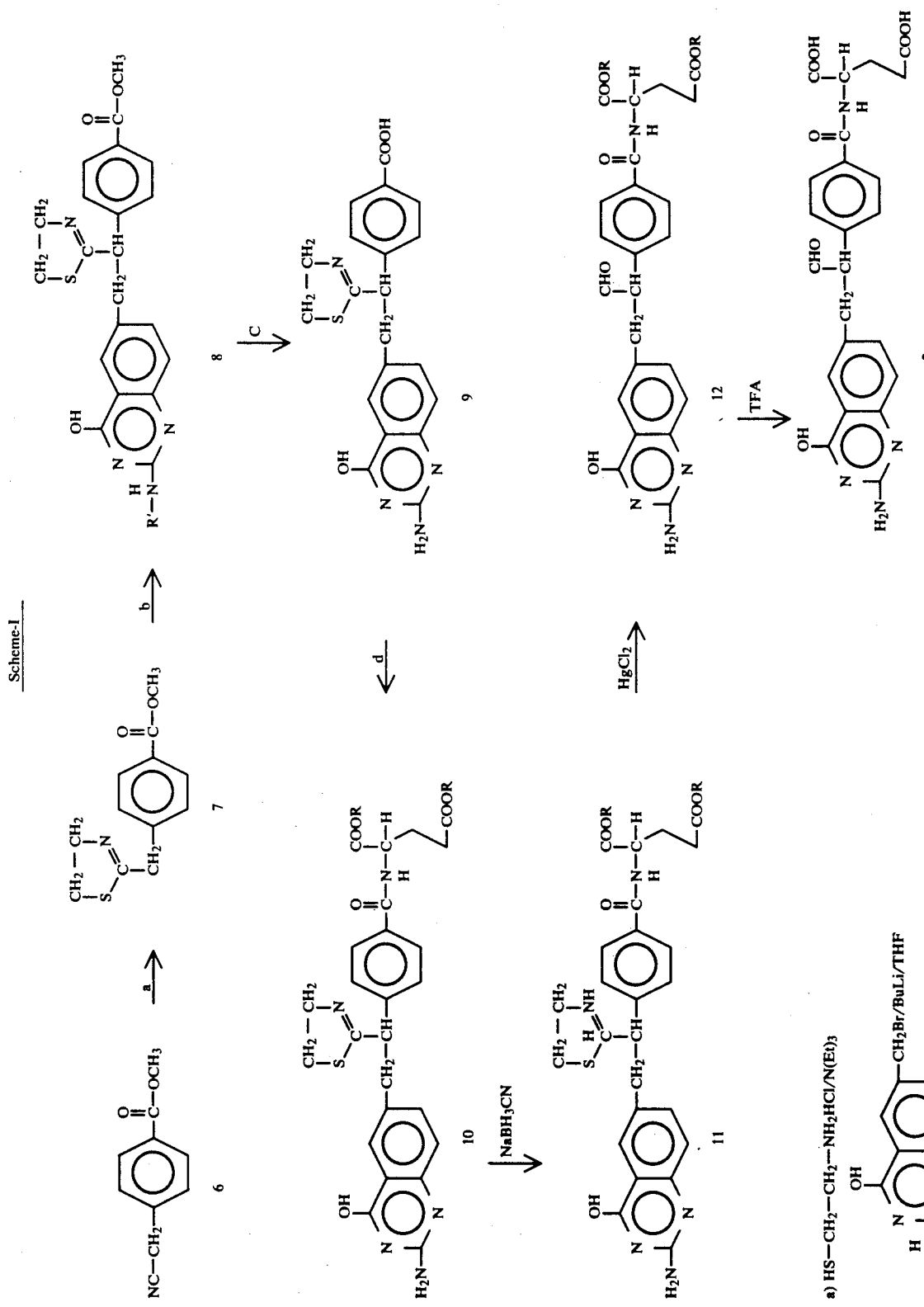

are analogues of 5-deazatetrahydrofolic acid, and all previously known powerful inhibitors of GARFTase that are folate analogues belong to this class of compounds.

This invention discloses the discovery of a new class of potent GARFTase inhibitors that are classical analogues of the folic acid processing a new 10-deaza-10-formyl pharmacophore. The inhibitors are derivatives of quinazolines, pteridines, or deazapteridines having the new pharmacophore. By analogy, several 10-deaza-10-formyl dihydro and tetrahydrofolate derivatives are also expected to be potent inhibitors of GARFTase and they are potential anticancer agents.

The representative compound of the present invention is 10-formyl-5,8,10-trideazatetrahydrofolic acid (FTDF) having the formula 1. FTDF, when assayed as an inhibitor of hog liver glycinamide ribonucleotide formyltransferase, exhibited an $I_{50}$ value of 0.15 μM. It inhibited the growth of SW480 colon adenocarcinoma cells at a concentration between 2 and 3 μgr/mL. Therefore, FTDF (1) should have clinical utility as a novel anticancer agent. This invention accordingly provides a process for treating leukemia, ascitic and solid tumors which comprises administering to a warm blooded animal with evidence of neoplastic disease a therapeutic nontoxic amount of FTDF (1) as such or in the form of a pharmacologically acceptable salt thereof. The compounds are also useful to treat autoimmune diseases such as rheumatoid arthritis, which are responsive to methotrexate.

The absolute configuration of the chiral carbon at the glutamate moiety of compounds 1 and 2 through 6 is (S) or L. The carbon at position 10 of compounds 1, and 2 through 6 is chiral leading to (R,S) and (S,S) diastereomers. This mixture of diasteromers can be therapeutically utilized directly or be separated, chromatographically so as to be in a form free of the other.

The process of this invention for the preparation of the representative compound FTDF (1) is illustrated in Scheme I and explained by Example I.

The process of the invention for the preparation of 10-formyl-5,8,10-trideazafolic acid (1) is a synthesis in which commercially available methyl-4(bromomethyl) benzoate is converted to the corresponding cyanomethyl derivative by reaction with NaCN using standard procedures. Conversion of the resulting methyl-4-(cyanomethyl) benzoate (6) to 2-(p-carbomethoxybenzyl) thiazoline (1) can be accomplished by refluxing 6 with cysteamine hydrochloride and triethylamine in ethanol. Other organic amines such as pyridine, trimethylamine, or bases such as sodium methoxide or lithium isopropylamide, may be used in this reaction. The solvent ethanol may be substituted with similar primary, secondary or tertiary alcohols, tetrahydrofuran, dioxane, or dimethyl formamide.

In the next stage of the synthesis, 2-(p-carbomethoxybenzyl) thiazoline (7) is reacted with 6-bromomethyl-2-pivaloylaminoquinazoline-4(3H)one (prepared according to the literature procedure of Acharya and Hynes, J. Heteroclic. Chem. 12,1283, 1975) in a non-protic solvent like tetrahydrofuran or 1,4-dioxane in presence of a strong base such as butyllithium, lithium diisopropylamide (LDA) or potassium-t-butoxide at a temperature range of 5° to −80° C. The resulting product, after workup and chromatographic purification is methyl-2-pivaloylamino-10-(2-thiazolyl)5,8,10-trideaza pterorate (8) which is then hydrolyzed using an inorganic base such as sodium hydroxide or potassium hydroxide and subsequently acidified to obtain the corresponding 10-(2-thiazolyl)5,8,10-trideazapteroie acid (9). The coupling of a diester of L-glutamic acid such as di-tert-butyl-L-glutamate to 9 can be performed, first by converting 9 to the corresponding mixed anhydride with a suitable alkyl chloroformate in a solvent such as THF or DMF in presence of a tertiary organic base, and the reacting the resulting mixed anhydride with a L-glutamate diester and subsequent workup. The resulting di-tert-butyl 10-(2-thiazolyl)5,8,10-trideafolate (10) is then reduced to the thiazolidinyl derivative 11 by treating with sodium cyanoborohydride (NaBH$_3$CN), aluminum amalgam or by catalytic hydrogenation. Other reducing agents such as sodium dithionite may also be employed for this reaction. Di-tert-butyl 10-formyl,5,8,10-trideazafolate (12) can be prepared from 11 by reductive transformation with HgCl$_2$ in a suitable aqueous organic solvent mixture such as acetonitrile/water.

The final stage of the synthesis is a procedure in which di-tert-butyl-10-formyl5,8,10-trideazafolate (12) is treated with an organic acid such as trifluoroacetic acid, or an inorganic acid such as methanolic hydrochloric acid to obtain the representative compound 10-formyl-5,8,10-trideazafolic acid (FTDF) (1). Final purification can be accomplished by ion exchange chromatography.

FTDF (1) exhibited very potent inhibitory activity against hog liver glycinamide ribonucleotide formyltransferase (GARFTase). The activity is almost twice as potent as that of the best known inhibitor. 5,8-dideazatetrahydrofolic acid (DDATHF) under identical experimental conditions (Table I).

TABLE I

| Inhibition of GAR-formyltransferase by FTDF and Analogues. | | |
|---|---|---|
| | $I_{50}$ (μM) | |
| Compound | GARFTase[a] | AICARFTase |
| 10-Formyl-5,8,10-trideazafolic acid (FTDF) | 0.150 (R,S) | 18.0 |
| 5-Deazaacyclotetrahydrofolic acid (5-DACTHF) | 2.50 | |
| 5,10-Dideazatetrahydrofolic acid (DDATHF) | 0.22 (R,S) | >500 |

[a]GAR-formyltransferase was purified and assayed as described by Daubner, S. C.; Young M.; Sammons, R. D.; Courtney, L. F.; Benkovic, S. F. Biochemistry 1986, 25, 2951-2957.

EXAMPLE 1

4-(Cyanomethyl)methylbenzoate (6)

To a solution of 9.16 g of (40 mmol) methyl 4-(bromomethyl) benzoate in 90 mL of CH$_3$OH was added dropwise to a solution of 3.9 g (80 mmol) of NaCN in 10 mL of water at room temperature. The reaction mixture was stirred overnight at room temperature and concentrated to ~20 mL. The solid thus formed were filtered, washed with water, and recrystallized from benzene: yield 5.8 g (83%); mp 61°-63° C. (Lit. 63°-64° C.); NMR(CDCl$_3$) δ8.15 (m, 2H, aromatic) 7.65 (m, 2H, aromatic) 4.10 (S, 2H, CH$_2$) 3.95 (S, 3H, CH$_3$); IR(Nujol) 2240 (CN) 1720 (ester) cm$^{-1}$. MS (M/Z) calculated for (C$_{10}$H$_9$NO$_2$, 175.00; found 175M+).

2-(p-Carbomethoxybenzyl) thiazoline (7)

To a solution of 1.75 g (10 mmol) of the above 4-(cyanomethyl) methyl benzoate (6) in 10 mL of EtOH was added 1.14 g (10 mmol) of cysteamine hydrochloride and 1.4 mL (10 mmol) of triethylamine. The reaction mixture was refluxed for 24 h. and evaporated to dryness. The residue was dissolved in CH$_2$Cl$_2$ (50 mL), washed with water and dried over Na$_2$SO$_4$. Removal of the solvent gave crude 7, which was crystallized from EtOH. Yield 2.1 g (89%); mp 67°-68° C.; NMR (CDCl$_3$), δ8.0 (m, 2H, aromatic), 7.4 (m, 2H, aromatic), 4.2 (t, 2H, CH$_2$), 3.9 (s, 3H CH$_3$), 3.85 (s, 2H, CH$_2$); IR (Nujol), 720 (ester), 1620 (C=N) cm$^{-1}$; MS (EI) calculated for (C$_{12}$H$_{13}$NO$_2$S), 235.00; found, 235 (M+).

Methyl-2-pivaloylamino-10-(2-thiazolyl)-5,8,10-trideazapteroate (8)

To a solution of 2.4 g (10 mmol) of the above 2-(p-carbomethoxybenzyl) thiazoline (7) in 30 mL of dry THF was added 4.28 mL of a 2.5M solution of BuLi in hexane at −78° C. The mixture was stirred for 2 h. at −78° C. and a solution of 3.0 g (9 mmol) of 2-pivaloylamino-6-bromomethylquinazolin-4(3H)-one prepared according to the procedure of Acharya and Hynes (J. Heterocycl. Chem 12,1283, 1975) in 30 mL of DMF was added dropwise via a syringe. The reaction mixture was stirred for an additional 2 h at −78° C. and slowly allowed to warm to 0° C. and stirred overnight. The resultant clear solution was neutralized with AcOH and evaporated. The residue was extracted with CH$_2$Cl$_2$, the extract washed with water, dried over Na$_2$SO$_4$ and filtered. Removal of the solvent from the filtrate gave crude 8, which was purified by chromatography on a silica gel column with 4% CH$_3$OH in CH$_2$Cl$_2$ as the eluent. Yield 1.75 g (40%); NMR (CDCl$_3$), δ8.0, 7.2 (m, 7H, aromatic), 4.28 (t, 2H CH$_2$CH$_2$), 3.9 (s, 3H, OCH$_3$), 3.6 (t, 1H, CH), 3.25 (t, 2H, CH$_2$CH$_2$), 2.9 (d, 2H, CH$_2$$^9$), 1.35 (s, 9H, t-Bu); MS (Cl) calculated for (C$_{26}$H$_{28}$N$_4$O$_4$S) 492.00; found, 493 (MH+).

10-(2-Thiazolyl)-5,8,10-trideazapteroic Acid (9)

To a solution of 1.48 g (3 mmol) of the above methyl-2-Pivaloylamino-10-(2-thiazolyl)5,8,10-trideazapteroate (8) in 45 mL of CH$_3$OH was added 45 mL of 0.2N NaOH. The reaction mixture was stirred at room temperature for 24 h, neutralized to pH 7 with 6N HCl and concentrated to about 40 mL under vacuum. The pH of the concentrate was adjusted to 4.0 with AcOH and the resulting precipitate was collected by filtration, washed with water and dried. Yield 875 mg (74%) mp>260° C. UV (0.1N NaOH) λmax 265 nm (ε11,494); 272 nm (ε11,423); λmin 326 nm (ε3,458); NMR (CDCl$_3$), δ8.15, 7.8, 7.5 (m, 7H aromatic), 4.55 (t, 2H, CH$_2$), 3.9 (c, 3H, CH$_2$, and CH), 3.0 (d, 2H, CH$_2$). MS (Cl) calculated for (C$_{20}$H$_{18}$N$_4$O$_3$S) 394.00; found, 394 (M+).

Di-tert-butyl 10-(2-thiazolyl)-5,8,10-trideazafolate (10)

To a mixture of 1.18 g (3 mmol) of the above 10-(2-thiazolyl)-5,8,10-trideazapterioc acid (9) in 100 mL of DMF was added 0.78 mL (7 mmol) of triethylamine. After cooling the solution to 0° C., 0.52 mL of freshly distilled isobutylchloroformate was added. The reaction mixture was stirred at 0°-5° C. for 2 h, 1.18 g (4.5 mmol) of di-t-butyl-L-glutamate was added and stirred at 25° C. for 24 h. The mixture was then concentrated under vacuum to a volume of ~10 mL, poured into ice-water (100 mL) and extracted with EtOAc. The extract was washed with water, dried over Na$_2$SO$_4$ and evaporated. The residue was chromatographed on a silica gel column with 4% CH$_3$OH in CH$_2$Cl$_2$ as the eluent. The appropriate fractions were pooled and concentrated to afford 1.40 g (74%) of the product; mp 100°-112° C.; IR (Nujol), 1730, (ester), 1620 (C=N); NMR (CDCl$_3$), δ7.8, 7.2 (2m, 7H aromatic), 4.3 (m, 3H, CH$_2$ of thiazolyl, αCH of glutamate), 3.5 (m, 3H, CH$^{10}$, and CH$_2$- of thiazolyl), 3.2 (d, 2H, CH$_2$$^9$), 2.3 (m, 2H, γ-CH$_2$ of glutamate), 2.2 (m, 2H, β-CH$_2$ of glutamate), 1.4 (s, 9H, t-Bu); 1.5 (s, 9H, t-Bu); MS (Cl) calculated for (C$_{33}$H$_{41}$N$_5$O$_6$S), 635.00; found, 635 (M+).

Di-tert-butyl 10-(2-thiazolidinyl)5,8,10-trideazafolate (11)

To a solution of 1.29 g (2.03 mmol) of the above di-tert-butyl 10-(2-thiazolyl)-5,8,10-trideazafolate (10) in 3 mL of CH$_3$OH were added 0.35 mL of 6N HCl and 220 mg (3.5 mmol) of NaBH$_3$CN at 0° C. After stirring for 2 h at 0° C., 0.35 mL of 6N HCl and 250 mg (3.98 mmol) of NaBH$_3$CN were added again and continued to stir for another 3 h at 0° C. The reaction mixture was poured into 400 mL of CH$_2$Cl$_2$, washed successively with 0.1N NaHCO$_3$ and distilled water, dried over Na$_2$SO$_4$, filtered, and evaporated. The residue was purified by chromatography on silica gel column with 5% CH$_3$OH in CH$_2$Cl$_2$ as the eluent. The desired fractions containing the major product were pooled and evaporated to afford 1.05 g (81%) of 11, mp 124°-126° C. MS (FAB+), calculated for (C$_{33}$H$_{43}$N$_5$O$_6$S), 637.00; found, 638 (MH+).

Di-tert-butyl 10-formyl-5,8,10-trideazafolate (12)

To a solution of 300 mg (1.1 mmol) of HgCl$_2$ in 5 mL of CH$_3$CN/H$_2$O (4:1) was added dropwise a solution of 540 mg (0.85 mmol) of the above di-tert-butyl 10-(2-thiazaolidinyl)5,8,10-trideazafolate (11) in 10 mL of CH$_3$CN/H$_2$O (4:1) at room temperature. The reaction mixture was stirred for 7 h, poured into water (50 mL) and extracted with EtOAc. The extract was washed successively with 10% Kl, 5% NaHCO$_3$ and distilled water, dried over Na$_2$SO$_4$ and filtered. Removal of the solvent gave the crude product which was purified by chromatography on silica gel column with 10% CH$_3$OH in CH$_2$Cl$_2$ as the eluent. The desired fractions were pooled and concentrated to afford 280 mg (57%) of 12. MS (FAB+), calculated for (C$_{31}$H$_{38}$N$_4$O$_7$), 578.00; found, 579 (MH+).

10-Formyl-5,8,10-trideazafolic Acid (1)

A mixture of 290 mg (0.05 mmol) of the above di-tert-butyl 10-formyl-5,8,10-trideazafolate (12) and 3 mL of CF$_3$COOH was stirred at room temperature for 3 h, and poured into Et$_2$O. The residue was triturated three times with Et$_2$O, dried and dissolved in 0.1M NaHCO$_3$. The pH of the solution was adjusted to 7.0 with 0.1N HCl and applied on a DEAE-cellulose column. The column was eluted with a linear NaCl gradient ranging from 0 to 0.5M in 0.005M phosphate buffer at pH 7.0. All the fractions corresponding to the product was pooled, concentrated to ~30 mL and acidified with 1N HCl to pH 3.5, whereupon a precipitate was formed, which was filtered, washed with water and dried. mp>280° C. Yield 30 mg (~11%); MS (FAB−) calculated for (C$_{23}$H$_{22}$N$_4$O$_7$), 466.00; found, 465 (M-H). UV (0.01N NaOH) λmax 251 nm (ε15,996), 263 nm (ε12,599); λmin 325 nm (ε6,072).

Having regard to the foregoing disclosure, the following is claimed as inventive and patentable embodiments thereof;

1. 10-Formyl-5,8,10-trideazafolic acid having the formula:

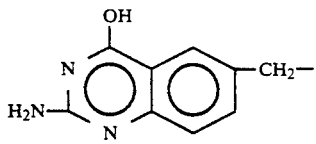

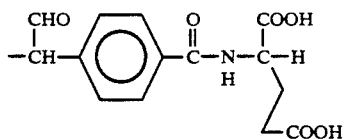

2. 2-Desamino-2-methyl-10-formyl-5,8,10-trideazafolic acid having the formula:

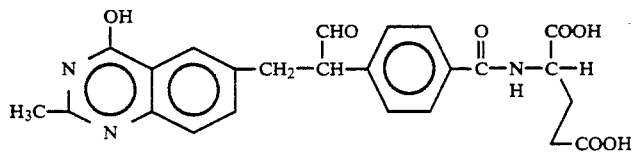

3. A pharmaceutical composition in dosage unit form for treating leukemia, ascites tumors or solid tumors comprising an amount within the range of about 0.1 to about 500 mg of 10-formyl-5,8,10-trideazafolic acid per dosage unit therapeutically effective to ameliorate leukemia, ascites tumors or solid tumors together with a pharmaceutically acceptable nontoxic carrier or diluent thereof.

4. A pharmaceutical composition in dosage unit form for treating leukemia, ascites tumors or solid tumors comprising an amount within the range of about 0.1 to about 500 mg of 2-desamino-2-methyl-10-formyl-5,8,10-trideazafolic acid per dosage unit therapeutically effective to ameliorate leukemia, ascites tumors or solid tumors together with a pharmaceutically acceptable nontoxic carrier or diluent thereof. thereof.

5. A process for treating leukemia, ascites tumors or solid tumors which comprises administering orally or parenterally to a warm blooded animal having an abnormal proportion of leukocytes or other evidence of malignancy, a therapeutic and relatively nontoxic amount of 10-formyl-5,8,10-trideazafolic acid to ameliorate leukemia, ascites tumors or solid tumors.

6. A process for treating leukemia, ascites tumors or solid tumors which comprises administering orally or parenterally to a warm blooded animal having an abnormal proportion of leukocytes or other evidence of malignancy, a therapeutic and relatively nontoxic amount of 2-desamino-2-methyl-10-formyl-5,8,10-trideazafolic acid to ameliorate leukemia, ascites tumors or solid tumors.

* * * * *